(12) United States Patent
Park et al.

(10) Patent No.: US 11,553,947 B2
(45) Date of Patent: Jan. 17, 2023

(54) SPINAL DEFORMITY SEQUENTIAL PERSUADER

(71) Applicant: Aesculap Implant Systems, LLC, Center Valley, PA (US)

(72) Inventors: Jacob Park, Center Valley, PA (US); Andrew Dauster, Center Valley, PA (US); Jeffrey S. Tompkins, Center Valley, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 558 days.

(21) Appl. No.: 16/513,082

(22) Filed: Jul. 16, 2019

(65) Prior Publication Data

US 2021/0015525 A1 Jan. 21, 2021

(51) Int. Cl.
*A61B 17/70* (2006.01)
*A61B 17/00* (2006.01)

(52) U.S. Cl.
CPC ...... *A61B 17/7086* (2013.01); *A61B 17/7088* (2013.01); *A61B 17/7001* (2013.01); *A61B 2017/00407* (2013.01)

(58) Field of Classification Search
CPC ............ A61B 17/7086; A61B 17/7085; A61B 17/7083; A61B 17/7088
See application file for complete search history.

(56) References Cited

U.S. PATENT DOCUMENTS

| | | | |
|---|---|---|---|
| 5,720,751 A | 2/1998 | Jackson | |
| 5,782,830 A | 7/1998 | Farris | |
| 5,910,141 A | 6/1999 | Morrison et al. | |
| 5,911,722 A | 6/1999 | Adler et al. | |
| 5,928,244 A | 7/1999 | Tovey et al. | |
| 5,935,133 A | 8/1999 | Wagner et al. | |
| 6,110,179 A | 8/2000 | Flivik et al. | |
| 6,139,551 A | 10/2000 | Michelson et al. | |
| 6,183,472 B1 | 2/2001 | Lutz | |
| 6,440,133 B1 | 8/2002 | Beale et al. | |
| 6,660,006 B2 | 12/2003 | Markworth et al. | |
| 6,682,533 B1 | 1/2004 | Dinsdale et al. | |
| 6,746,449 B2 | 6/2004 | Jones et al. | |
| 6,790,209 B2 | 9/2004 | Beale et al. | |
| 7,278,995 B2 | 10/2007 | Nichols et al. | |
| 7,470,279 B2 | 12/2008 | Jackson | |
| 7,491,207 B2 | 2/2009 | Keyer et al. | |
| 7,520,879 B2 | 4/2009 | Justis et al. | |
| 7,608,081 B2 | 10/2009 | Abdelgany | |
| 7,771,430 B2 | 8/2010 | Jones et al. | |

(Continued)

*Primary Examiner* — Julianna N Harvey

(74) *Attorney, Agent, or Firm* — Christopher A. Rothe; Culhane Meadows, PLLC

(57) ABSTRACT

A persuader instrument for advancing a fixation rod into a vertebral implant includes a housing and at least one arm. The at least one arm can include detents for detachable connection to the vertebral implant. The persuader instrument can also include a shaft coupled to an anchor. The anchor can include a fixation rod engagement surface. The shaft can be axially displaceable through the housing to axially displace the anchor and a rod engaged by the anchor. The persuader instrument can further include an auto-locking ratchet assembly in releasable engagement with the shaft. The auto-locking ratchet assembly can control axial displacement of the shaft through the longitudinal passage of the housing.

27 Claims, 10 Drawing Sheets

(56) References Cited

U.S. PATENT DOCUMENTS

| | | |
|---|---|---|
| 7,776,040 B2 | 8/2010 | Markworth et al. |
| 7,824,411 B2 | 11/2010 | Varieur et al. |
| 7,824,413 B2 | 11/2010 | Varieur et al. |
| 7,842,044 B2 | 11/2010 | Runco et al. |
| 7,862,587 B2 | 1/2011 | Jackson |
| 7,887,541 B2 | 2/2011 | Runco et al. |
| 7,909,835 B2 | 3/2011 | Oribe et al. |
| 7,922,749 B2 | 4/2011 | Dewey |
| 7,931,654 B2 | 4/2011 | Jones et al. |
| 7,931,677 B2 | 4/2011 | Abdelgany |
| 7,985,242 B2 | 7/2011 | Forton et al. |
| 8,142,436 B2 | 3/2012 | Kirschman |
| 8,172,847 B2 | 5/2012 | Dziedzic et al. |
| 8,192,438 B2 | 6/2012 | Garamszegi |
| 8,246,623 B2 | 8/2012 | Peultier et al. |
| 8,303,595 B2 | 11/2012 | Jones |
| 8,308,729 B2 | 11/2012 | Nunley et al. |
| 8,308,774 B2 | 11/2012 | Hoffman et al. |
| 8,317,796 B2 | 11/2012 | Stihl et al. |
| 8,343,160 B2 | 1/2013 | Techiera et al. |
| 8,377,104 B2 | 2/2013 | Jones et al. |
| 8,398,644 B2 | 3/2013 | Kirschman |
| 8,439,922 B1 | 5/2013 | Arnold et al. |
| RE44,296 E | 6/2013 | Beale et al. |
| 8,500,750 B2 | 8/2013 | Varieur et al. |
| 8,540,718 B2 | 9/2013 | Dauster et al. |
| 8,545,505 B2 | 10/2013 | Sandstrom et al. |
| 8,579,943 B2 | 11/2013 | Nichols et al. |
| 8,591,515 B2 | 11/2013 | Jackson |
| 8,603,094 B2 | 12/2013 | Walker et al. |
| 8,608,746 B2 | 12/2013 | Kolb et al. |
| 8,617,165 B2 | 12/2013 | Harper et al. |
| 8,636,742 B2 | 1/2014 | Runco et al. |
| RE44,813 E | 3/2014 | Beale et al. |
| 8,685,029 B2 | 4/2014 | Dziedzic et al. |
| 8,690,879 B2 | 4/2014 | Kirschman et al. |
| 8,764,754 B2 | 7/2014 | Butler et al. |
| 8,764,756 B2 | 7/2014 | Jones et al. |
| 8,834,474 B2 | 9/2014 | Jones et al. |
| 8,845,649 B2 | 9/2014 | Jackson |
| 8,864,767 B2 | 10/2014 | Blain et al. |
| 8,894,657 B2 | 11/2014 | Jackson |
| 8,894,662 B2 | 11/2014 | Varieur et al. |
| 8,900,240 B2 | 12/2014 | White et al. |
| 8,961,523 B2 | 2/2015 | Barrus et al. |
| 9,005,204 B2 | 4/2015 | Manninen et al. |
| 9,101,416 B2 | 4/2015 | Dunbar et al. |
| 9,050,143 B2 | 6/2015 | May et al. |
| 9,066,761 B2 | 6/2015 | McBride et al. |
| 9,078,709 B2 | 7/2015 | McBride |
| 9,084,642 B2 | 7/2015 | Peultier |
| 9,125,694 B2 | 9/2015 | Butler et al. |
| 9,149,307 B2 | 10/2015 | Sandstrom et al. |
| 9,161,788 B2 | 10/2015 | Daubs et al. |
| 9,198,698 B1 | 12/2015 | Doose et al. |
| 9,204,909 B2 | 12/2015 | Rezach et al. |
| 9,216,043 B2 | 12/2015 | Stad et al. |
| 9,247,969 B2 | 2/2016 | Nunley et al. |
| 9,265,533 B2 | 2/2016 | Nelson et al. |
| 9,265,534 B2 | 2/2016 | Jackson |
| 9,265,536 B2 | 2/2016 | Jackson |
| 9,433,446 B2 | 9/2016 | McLean et al. |
| 9,452,000 B2 | 9/2016 | Barrus |
| 9,468,474 B2 | 10/2016 | Parikh et al. |
| 9,468,476 B2 | 10/2016 | Boachie-Adjei et al. |
| 9,480,505 B2 | 11/2016 | Hutchens |
| 9,486,256 B1 | 11/2016 | Lish et al. |
| 9,486,257 B2 | 11/2016 | Smith et al. |
| 9,492,208 B1 | 11/2016 | Arnold et al. |
| 9,517,099 B2 | 12/2016 | Bess et al. |
| 9,526,537 B2 | 12/2016 | Meyer et al. |
| 9,532,814 B2 | 1/2017 | Harper et al. |
| 9,532,815 B2 | 1/2017 | Jackson |
| 9,532,816 B2 | 1/2017 | Barrus et al. |
| 9,629,661 B2 | 4/2017 | Kraus |
| 9,636,151 B2 | 5/2017 | Jackson |
| 9,636,152 B2 | 5/2017 | Daubs et al. |
| 9,649,140 B1 | 5/2017 | Doose et al. |
| 9,655,659 B2 | 5/2017 | Black et al. |
| 9,655,664 B2 | 5/2017 | Barrus et al. |
| 9,668,789 B2 | 6/2017 | Barrett et al. |
| 9,717,531 B2 | 8/2017 | Anand et al. |
| 9,814,498 B2 | 11/2017 | Seelig |
| 9,901,378 B2 | 2/2018 | Dauster et al. |
| 9,918,752 B2 | 3/2018 | Hennard et al. |
| 9,936,986 B2 | 4/2018 | Butler et al. |
| 9,943,343 B2 | 4/2018 | Meyer et al. |
| 9,943,344 B2 | 4/2018 | Mladenov et al. |
| 9,962,196 B2 | 5/2018 | McLean et al. |
| 9,962,198 B2 | 5/2018 | Daubs et al. |
| 9,987,054 B2 | 6/2018 | Jackson |
| 10,028,775 B2 | 7/2018 | Iott et al. |
| 10,034,689 B2 | 7/2018 | Barrus et al. |
| 10,064,662 B2 | 9/2018 | Gunn et al. |
| 10,085,778 B2 | 10/2018 | Semingson et al. |
| 10,136,927 B1 | 11/2018 | Lish et al. |
| 10,154,862 B2 | 12/2018 | Miller et al. |
| 10,238,435 B2 | 3/2019 | Seelig |
| 10,245,082 B2 | 4/2019 | Parker et al. |
| 2004/0147937 A1 | 7/2004 | Dunbar et al. |
| 2004/0254576 A1 | 12/2004 | Dunbar et al. |
| 2004/0267275 A1 | 12/2004 | Cournoyer et al. |
| 2005/0004573 A1 | 1/2005 | Abdou |
| 2005/0131419 A1 | 6/2005 | McCord et al. |
| 2005/0131420 A1 | 6/2005 | Techiera et al. |
| 2005/0149048 A1 | 7/2005 | Leport et al. |
| 2005/0192587 A1 | 9/2005 | Lim |
| 2005/0228392 A1 | 10/2005 | Keyer et al. |
| 2006/0036254 A1 | 2/2006 | Lim |
| 2006/0036260 A1 | 2/2006 | Runco et al. |
| 2006/0074418 A1 | 4/2006 | Jackson |
| 2006/0106394 A1 | 5/2006 | Colleran |
| 2006/0276798 A1* | 12/2006 | Lim ............... A61B 17/7086 606/86 R |
| 2008/0228233 A1* | 9/2008 | Hoffman ......... A61B 17/7088 606/86 A |
| 2009/0018593 A1* | 1/2009 | Barrus ............ A61B 17/7086 |
| 2015/0100097 A1* | 4/2015 | Barrus ............ A61B 17/7085 606/86 A |
| 2015/0100098 A1* | 4/2015 | Moore ............ A61B 17/7086 606/86 A |
| 2016/0206354 A1* | 7/2016 | Mladenov ....... A61B 17/7002 |
| 2016/0331420 A1 | 11/2016 | Dandanopoulos et al. |
| 2017/0189083 A1 | 7/2017 | Barrett et al. |
| 2017/0209154 A1 | 7/2017 | Krause et al. |
| 2017/0252074 A1* | 9/2017 | Semingson ...... A61B 17/7091 |
| 2017/0319246 A1* | 11/2017 | Mladenov ....... A61B 17/7086 |
| 2017/0325855 A1 | 11/2017 | Roger et al. |
| 2017/0325856 A1 | 11/2017 | George |
| 2018/0049781 A1* | 2/2018 | Heuer ............. A61B 17/7086 |
| 2018/0055545 A1* | 3/2018 | Biedermann ..... A61B 17/7037 |
| 2018/0140337 A1 | 5/2018 | Noordeen et al. |
| 2018/0185072 A1 | 7/2018 | Rubin et al. |
| 2018/0199964 A1 | 7/2018 | Min et al. |
| 2018/0221065 A1 | 8/2018 | Mladenov et al. |
| 2018/0235676 A1 | 8/2018 | Butler et al. |
| 2018/0250039 A1 | 9/2018 | Jackson |
| 2018/0303516 A1 | 10/2018 | Barrus et al. |
| 2018/0303517 A1 | 10/2018 | Barrus et al. |
| 2018/0338781 A1 | 11/2018 | Gunn et al. |
| 2018/0360504 A1 | 12/2018 | Cain et al. |
| 2019/0069934 A1 | 3/2019 | Mickiewicz et al. |
| 2019/0083149 A1 | 3/2019 | Sandstrom et al. |
| 2019/0090916 A1 | 3/2019 | Harper |
| 2019/0117280 A1 | 4/2019 | Avidano et al. |

* cited by examiner

SPINAL DEFORMITY SEQUENTIAL PERSUADER

FIELD

The present disclosure relates generally to instruments for correcting spinal deformities and more particularly to an instrument for repositioning a vertebral body into alignment with a fixation rod.

BACKGROUND

Spinal fixation systems may be used in surgery to align, adjust and/or fix portions of the spinal column, i.e., vertebrae, in a desired spatial relationship relative to each other. Many spinal fixation systems employ a spinal fixation rod for supporting the spine and for properly positioning components of the spine for various treatment purposes. The fixation rod, which is generally formed of a metal, such as cobalt chrome or titanium, can be implanted to correct deformities, prevent movement of vertebral bodies relative to each other, or for other purposes. Vertebral anchors, comprising pins, bolts, screws, and hooks, engage the vertebrae and connect the rod to different vertebrae.

Adult Spinal Deformity (ASD) refers to a number of conditions of the spine in which the spinal curvature is outside of defined normal limits. In some patients, the spinal curvature can be adjusted by repositioning or reorienting each vertebral body so that the vertebrae align with the curvature of a fixation rod.

SUMMARY

Various terms will be used throughout the application to describe different features, and will be defined as follows, unless otherwise indicated.

The terms "proximal", "proximally" and the like, as used herein, refer to a location or position toward the user of the instrument when the instrument is in use.

The terms "distal", "distally" and the like, as used herein, refer to a location or position toward the patient when the instrument is in use.

The terms "axial", "axially", "longitudinal", "longitudinally" and the like refer to a direction or dimension that is parallel to the longest dimension of an object.

Instruments according to the present disclosure can be used with various types of vertebral anchors and implants. The examples described herein will be described in conjunction with polyaxial screw assemblies, with the understanding that polyaxial screw assemblies are just one type of vertebral anchor that can be used with instruments according to the present disclosure.

In one aspect of the present disclosure, an instrument for correcting spinal deformities includes a persuader instrument for advancing a fixation rod into a rod receiving channel of a vertebral implant.

In another aspect of the present disclosure, a persuader instrument includes a housing having a proximal housing end and a distal housing end. The housing can define a longitudinal passage extending between the proximal housing end and distal housing end. The housing can further define a longitudinal axis extending through the longitudinal passage.

In another aspect of the present disclosure, a persuader instrument includes a first arm and a second arm, the first and second arms including detents configured for detachable connection to a vertebral implant.

In another aspect of the present disclosure, a persuader instrument includes an anchor comprising a fixation rod engagement surface.

In another aspect of the present disclosure, a persuader instrument includes a shaft having a proximal shaft end and a distal shaft end, the distal shaft end coupled to an anchor in an axially fixed but rotatable connection, with the shaft being axially displaceable through a longitudinal passage of a housing to axially displace the anchor.

In another aspect of the present disclosure, a persuader instrument includes an auto-locking ratchet assembly in releasable engagement with a shaft, the auto-locking ratchet assembly operable to control axial displacement of the shaft through a longitudinal passage of a housing.

In another aspect of the present disclosure, a persuader instrument includes an auto-locking ratchet assembly that includes at least one ratcheting block that releasably engages a shaft.

In another aspect of the present disclosure, a persuader instrument includes at least one ratcheting block that includes a first ratchet surface, and a shaft includes a second ratchet surface in releasable engagement with the first ratchet surface.

In another aspect of the present disclosure, a persuader instrument includes a ratchet surface with a plurality of ledges separated by inclined faces, and another ratchet surface with a plurality of undercuts separated by ramps.

In another aspect of the present disclosure, a persuader instrument includes a ratcheting block that is radially displaceable relative to a longitudinal axis between a ratcheting position in which a first ratchet surface matingly engages with a second ratchet surface, and a release position, in which the first ratchet surface is radially separated and disengaged from the second ratchet surface.

In another aspect of the present disclosure, a persuader instrument includes a plurality of ledges that axially abut a plurality of undercuts when the a ratcheting block is in the ratcheting position to prevent a shaft from moving toward the proximal housing end.

In another aspect of the present disclosure, a persuader instrument includes an auto-locking ratchet assembly with at least one release button, the at least one release button in slidable engagement with at least one ratcheting block to toggle the at least one ratcheting block between a ratcheting position and a release position.

In another aspect of the present disclosure, a persuader instrument includes at least one spring element in engagement with at least one ratcheting block, the at least one spring element disposed between a housing and the at least one ratcheting block under stored energy that exerts a biasing force on the at least one ratcheting block to urge the at least one ratcheting block toward a ratcheting position.

In another aspect of the present disclosure, a persuader instrument includes at least one release button movable to a depressed position to move at least one ratcheting block to a release position against a biasing force of a spring element.

In another aspect of the present disclosure, a persuader instrument includes at least one release button with a first abutment surface and at least one ratcheting block with a second abutment surface that slidingly engages the first abutment surface.

In another aspect of the present disclosure, a persuader instrument includes at least one release button with a first portion that projects outside of a housing and a second portion that extends into a longitudinal passage into engagement with at least one ratcheting block.

In another aspect of the present disclosure, a persuader instrument includes at least one ratcheting block that can be moved to a ratcheting position, in which a shaft can be axially displaced toward a proximal end of a housing and toward a distal end of the housing in response to rotation of the shaft relative to the housing.

In another aspect of the present disclosure, a persuader instrument includes at least one ratcheting block that can be moved to a ratcheting position, in which a shaft can be axially displaced toward a distal housing end in response to axial force applied to the shaft, but is locked against axial displacement toward the proximal housing end in response to axial force.

In another aspect of the present disclosure, a persuader instrument includes first and second ratchet surfaces that include threads.

In another aspect of the present disclosure, a persuader instrument includes first and second ratchet surfaces that include ratchet teeth that follow a saw tooth configuration.

In another aspect of the present disclosure, a persuader instrument includes first and second ratchet surfaces that include a first section having threads and a second section having ratchet teeth that follow a saw tooth configuration.

In another aspect of the present disclosure, a persuader instrument includes at least one arm that is pivotable radially outwardly from a longitudinal axis to an open position, and pivotable radially inwardly toward the longitudinal axis to a closed position.

In another aspect of the present disclosure, a persuader instrument includes at least one arm connected to a housing by a hinge comprising a pivot spring element, the pivot spring element connected between the housing and the at least one arm under stored energy that biases the at least one arm toward a closed position.

In another aspect of the present disclosure, a persuader instrument includes a first arm having a first rod guiding surface and a second arm having a second rod guiding surface, the first and second rod guiding surfaces converging inwardly toward a longitudinal axis.

In another aspect of the present disclosure, a persuader instrument includes first and second rod guiding surfaces having rounded sections.

In another aspect of the present disclosure, a persuader instrument includes an anchor having a frame portion arranged around first and second arms.

In another aspect of the present disclosure, a persuader instrument includes an anchor axially displaceable between a raised position and a lowered position, the frame portion being positioned closer to the detents in the lowered position to apply a radially inward clamping force to distal ends of the first and second arms.

In another aspect of the present disclosure, a persuader instrument includes first and second arms having rail portions on which the frame portion of the anchor is slidably arranged, and detent portions having detents, the detent portions arranged radially inwardly relative to the rail portions.

In another aspect of the present disclosure, a persuader instrument includes an anchor with one or more polylocking features.

In another aspect of the present disclosure, a persuader instrument includes an anchor with one or more anti-splaying elements.

In another aspect of the present disclosure, a persuader instrument includes a first arm and a second arm with one or more anti-splaying features that cooperate with one or more anti-splaying elements of an anchor.

Any combination and subcombination of the foregoing aspects are contemplated in accordance with the present disclosure.

BRIEF DESCRIPTION OF THE DRAWINGS

The foregoing summary and the following detailed description will be better understood in conjunction with non-limiting examples shown in the drawing figures, of which.

DETAILED DESCRIPTION

Figure 1:
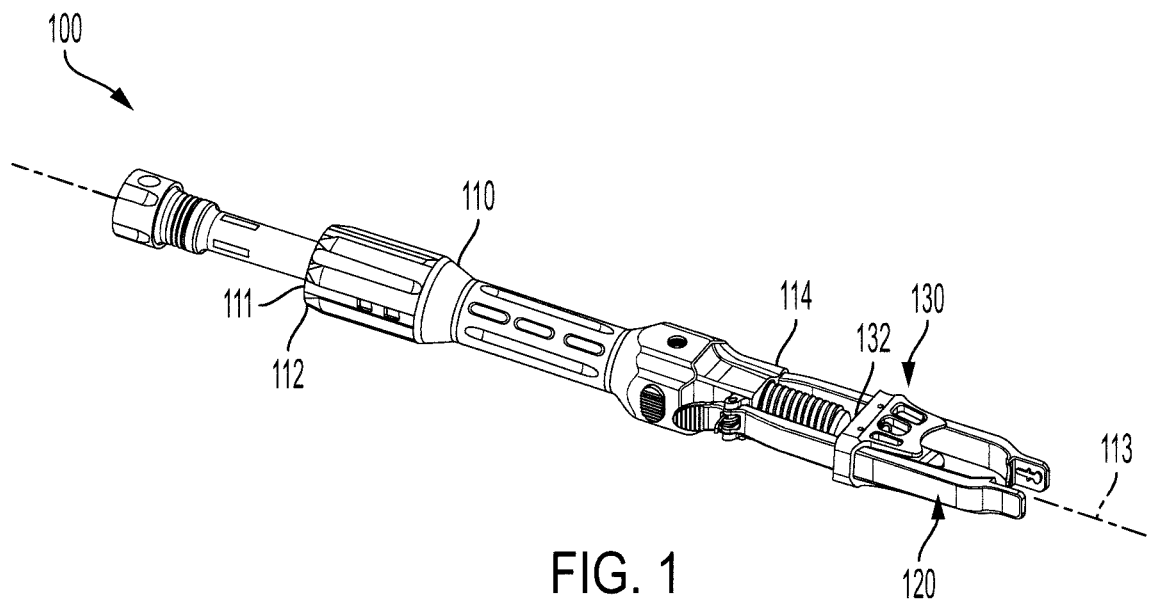
FIG. 1 is a perspective view of a sequential rod persuader instrument according to one example.

Referring to FIG. 1, a sequential rod persuader instrument or "rod persuader" 100 is shown according to one example. Rod persuader 100 is configured to advance a fixation rod into a seated position in a polyaxial screw assembly. To advance the fixation rod into the seated position, rod persuader 100 is mounted onto a polyaxial screw assembly that is implanted in the vertebral body. Once rod persuader 100 is mounted onto the polyaxial screw assembly and over the fixation rod, a surgeon can use the rod persuader to advance the fixation rod down into the polyaxial screw assembly, where it can be locked in place to secure the vertebral body to the fixation rod.

Figure 2:
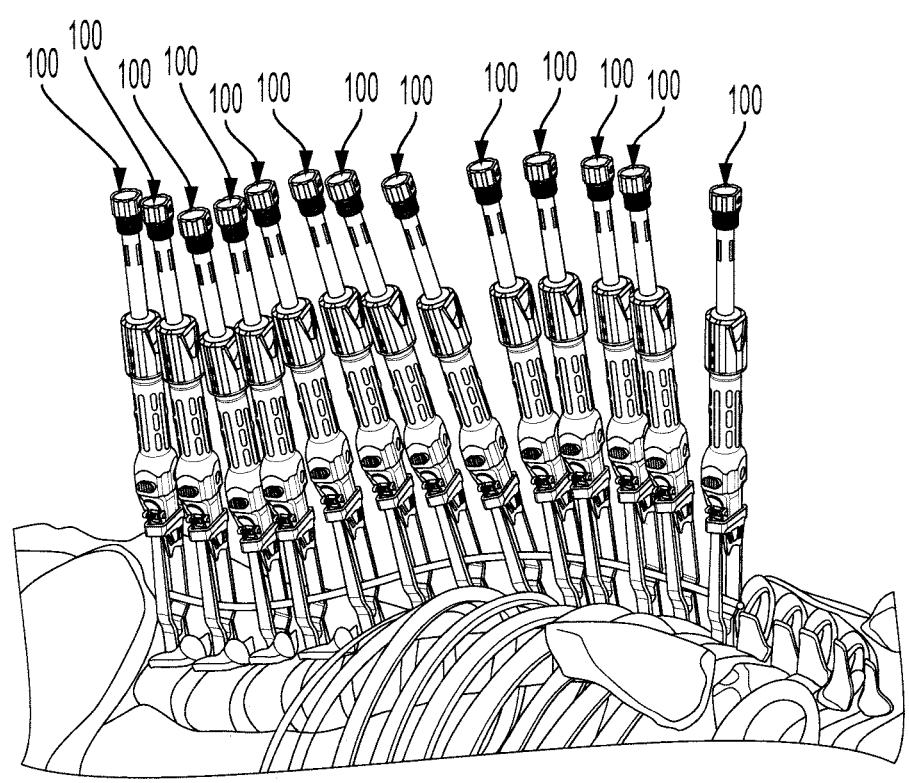
FIG. 2 is a schematic view of a section of the spine instrumented with a series of rod persuader instruments according to FIG. 1.
Figure 3:
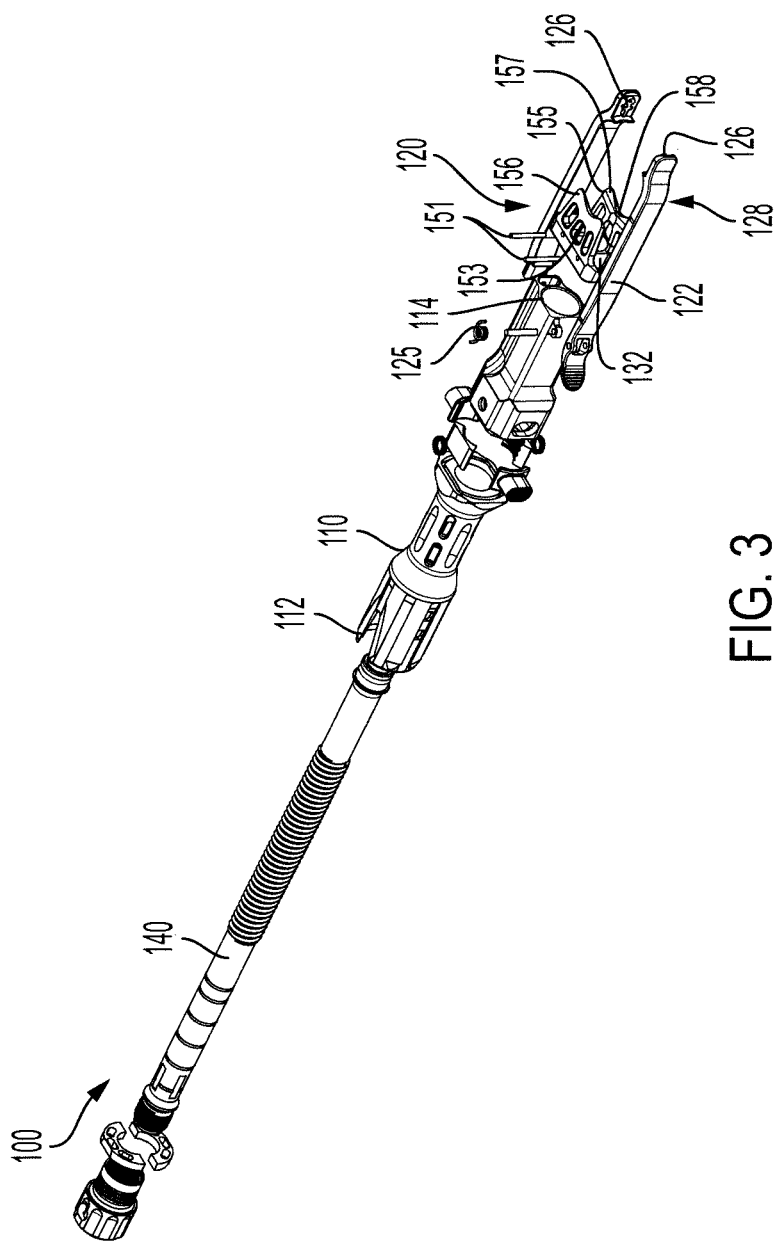
FIG. 3 is an exploded perspective view of the rod persuader instrument according to FIG. 1.

Adjusting the curvature of the spine requires the adjustment of multiple vertebrae. After one vertebral body is adjusted relative to a fixation rod, the progress made with that adjustment must be maintained while adjustments are made to other vertebral bodies. Therefore, rod persuaders according to the present disclosure are designed to adjust the position of a vertebral body and hold the adjusted position while an adjacent vertebral body is repositioned. This "sequential" persuasion can be accomplished by attaching one rod persuader to each vertebral body being adjusted. FIG. 2 shows a spine fully instrumented with a series of rod persuaders 100 mounted to a series of polyaxial screw assemblies.

Rod persuader 100 includes an elongated tubular housing 110. Housing 110 has a proximal housing end 112 and a distal housing end 114 opposite the proximal housing end. Housing 110 defines a longitudinal passage 111 extending between proximal housing end 112 and distal housing end 114. Housing 110 further defines a longitudinal axis 113 extending through longitudinal passage 111.

Referring now to FIGS. 3-6, distal housing end 114 is attached to a vertebral anchor clamping assembly 120. Clamping assembly 120 includes a first arm 122 and a second arm 124. First and second arms 122, 124 are operable to clamp onto a polyaxial screw assembly. In particular, first and second arms 122, 124 are configured to clamp onto attachment features on a rod receiving component of a polyaxial screw assembly to secure rod persuader 100 to the polyaxial screw assembly.

Figure 7:
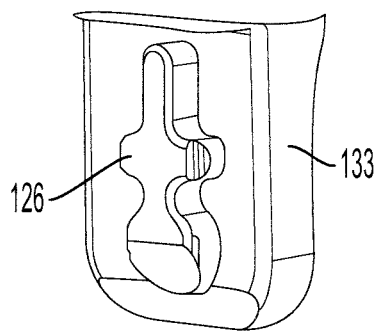
FIG. 7 is an enlarged truncated perspective view of an engagement element on the rod persuader instrument according to FIG. 1.

A variety of attachment mechanisms according to the present disclosure can be used to attach rod persuaders to polyaxial screw assemblies. In the present example, first and second arms 122, 124 each have an irregularly shaped detent tab 126, as shown in FIG. 7. Each detent tab 126 is configured to be detachably mounted into a similarly-shaped cut-out in a rod receiving component of a polyaxial screw assembly.

Referring back to FIGS. 5 and 6, first and second arms 122, 124 each have an offset or "dog leg" configuration. The dog leg is configuration defined by a rail section 131 and a detent section 133 laterally offset from the rail section. When first and second arms 122, 124 are assembled with the rest of rod persuader 100, each detent sections 133 is positioned radially inwardly toward longitudinal axis 113, relative to its associated rail section 131. First and second arms 122, 124 form a gap 128 between them that creates a funnel or rod-centering structure, as will be explained.

Figure 4:
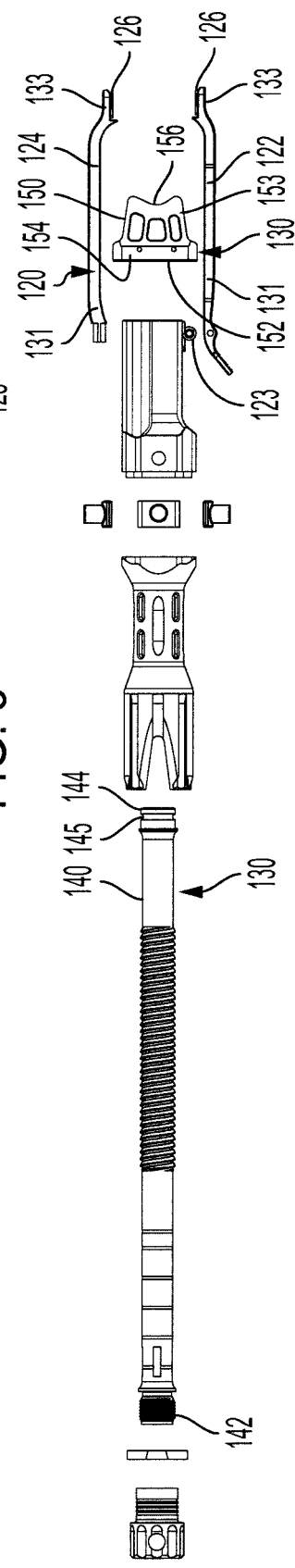
FIG. 4 is an exploded plan view of the rod persuader instrument according to FIG. 1.

Referring to FIGS. 1 and 4, rod persuader 100 has a rod persuading assembly 130 that is operable to displace a fixation rod relative to a rod receiving component of a polyaxial screw assembly. Rod persuading assembly 130 includes an elongated shaft 140 coupled to an anchor 150. Shaft 140 is axially displaceable through housing 110 to axially displace anchor 150 relative to first and second arms 122, 124. Shaft 140 includes a proximal shaft end 142 and a distal shaft end 144. Distal shaft end 144 is coupled to anchor 150 in an axially fixed but rotatable connection 132. A variety of axially fixed but rotatable configurations can be used. In the present example, distal shaft end 144 has an annular groove 145. A pair of pins 151 extend through holes in anchor 150 and reside in annular groove 145, one on each side of shaft 140, such that distal shaft end 144 is positioned between pins 151. In this arrangement, pins 151 connect distal shaft end 144 to anchor 150 in an axially fixed connection that allows shaft 140 to rotate relative to anchor 150.

When first and second arms 122, 124 are clamped onto the polyaxial screw assembly, rod persuader 100 is designed to apply force in the proximal direction on the polyaxial screw assembly via detent tabs 126, while applying distal force on the fixation rod via anchor 150. This has the effect of displacing the rod receiving component relative to the rod until the polyaxial screw assembly and the associated vertebral body are aligned with the rod.

Figure 5:
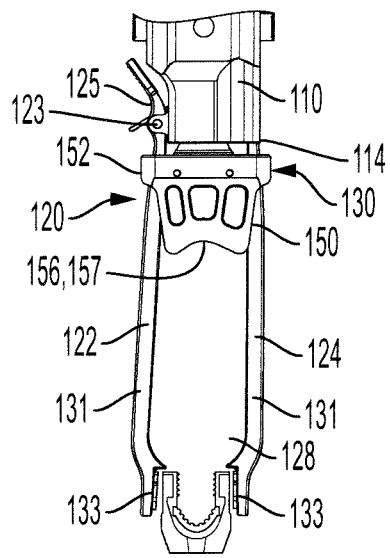
FIG. 5 is an enlarged truncated side view of a distal end of the rod persuader instrument according to FIG. 1, with pivot arms shown in a first operative state over a polyaxial screw assembly.
Figure 6:
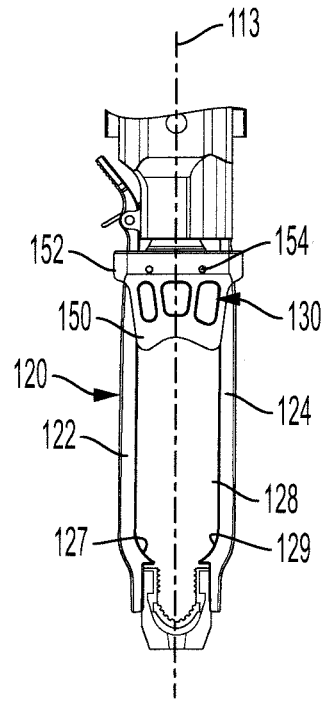
FIG. 6 is an enlarged truncated side view of a distal end of the rod persuader instrument according to FIG. 1, with pivot arms shown in a second operative state over a polyaxial screw assembly.

Referring to FIGS. 1, 5 and 6, anchor 150 has a proximal end that defines a frame portion 152. Frame portion 152 forms a rectangular brace or sleeve 154 that surrounds first and second clamping arms 122, 124. A first flange 153 and a second flange 155 extend distally from sleeve 154 and parallel to one another. First flange 153 has a distal edge 156 with a concave curvature, and second flange 155 has a distal edge 157 with a concave curvature. Distal edges 156, 157 collectively form a rod engagement surface 158 configured to engage a rod at two locations.

Figures 9, 10:
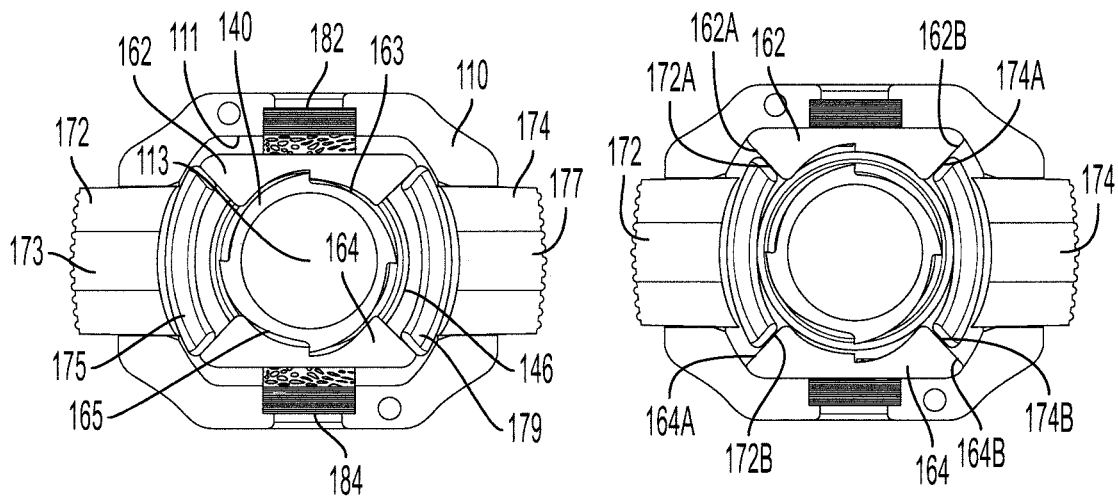
FIG. 9 is a top view of the ratchet assembly of FIG. 8, with components shown in a first operative state.
FIG. 10 is a top view of the ratchet assembly of FIG. 8, with components shown in a second operative state.

Rod persuader 100 features a first device configuration and a second device configuration that regulate how the rod persuading assembly 130 operates. These device configurations are illustrated in FIGS. 9 and 10, and will be explained in greater detail in subsequent paragraphs. The first and second device configurations differ in how they permit axial movement of shaft 140 relative to housing 110. The first device configuration provides a mechanical advantage when needed to move shaft 140 in the distal direction. In addition, the first device configuration provides a ratcheting function that maintains the position of shaft 140 after the shaft is advanced in the distal direction. The second device configuration provides a freely movable arrangement for shaft 140 when mechanical advantage and ratcheting are not needed. The first and second device configurations will now be explained in more detail.

When rod persuading assembly 130 advances a fixation rod into a rod receiving component, the rod can exert a significant amount of resistance to displacement and bear upwardly against anchor 150. Therefore, rod persuader 100 must be able to apply a significant amount of force against the rod to overcome the resistance against anchor 150 and displace the rod. Rod persuader 100 must also be able to maintain the advanced position of the rod after displacement and not allow any reverse movement in the proximal direction in response to resistance from the rod. These requirements are met by the first device configuration, which can apply a significant force against the rod by mechanical advantage, and maintain that force against the rod. Thus, the first device configuration allows axial displacement of shaft 140 relative to housing 110 to be controlled so that the shaft and anchor 150 can move distally as needed to advance the rod, while not move proximally in response to upward resistance from the rod.

At other times, there is not a need to control axial displacement of shaft 140 relative to housing 110. In fact, it is desirable at certain times for shaft 140 to move freely and easily in the proximal direction and distal direction. For example, free axial movement of shaft 140 can be desirable when rod persuader 100 is first being attached to a polyaxial screw assembly, or when the rod persuader is being removed from a polyaxial screw assembly after the fixation rod is locked in the polyaxial screw assembly by a locking element. Such freedom of movement in the axial direction is provided by the second device configuration, which allows shaft 140 and anchor 150 to move freely relative to housing 110 when strict control over axial displacement is not needed.

The first and second device configurations are manually set by the user using a ratchet assembly 160. The terms "ratchet" and "ratcheting", as used herein, refer to any assembly in which two or more objects interface with one another by means of interlocking surfaces that allow relative movement in one direction but prevent movement in the opposite direction. Examples of ratchet or ratcheting assemblies according to the present disclosure include but are not limited to surfaces with helical threads, saw teeth, a combination of threads and saw teeth, or other projections that matingly engage one another.

Figure 8:
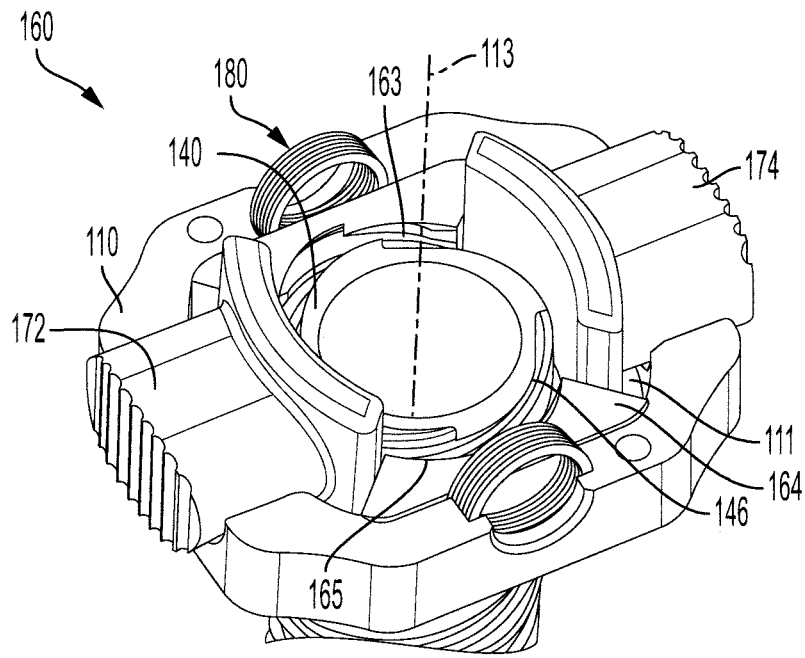
FIG. 8 is an enlarged truncated perspective view of a ratchet assembly of the rod persuader instrument according to FIG. 1.

A user can manually set the first device configuration by engaging ratchet assembly 160, and manually set the second device configuration by disengaging the ratchet assembly. Referring now to FIGS. 8-10, ratchet assembly 160 includes a first ratcheting block 162 and a second ratcheting block 164 that is diametrically opposed to the first ratcheting block relative to longitudinal axis 113. First and second ratcheting blocks 162, 164 have first ratchet surfaces 163, 165 respectively. Shaft 140 has a second ratchet surface 146. First ratchet surfaces 163, 165 are movable into and out of mating engagement with second ratchet surface 146 when the ratchet assembly is engaged and disengaged, respectively. First ratchet surfaces 163, 165 and second ratchet surface 146 each consist of a helical thread.

Figure 11:
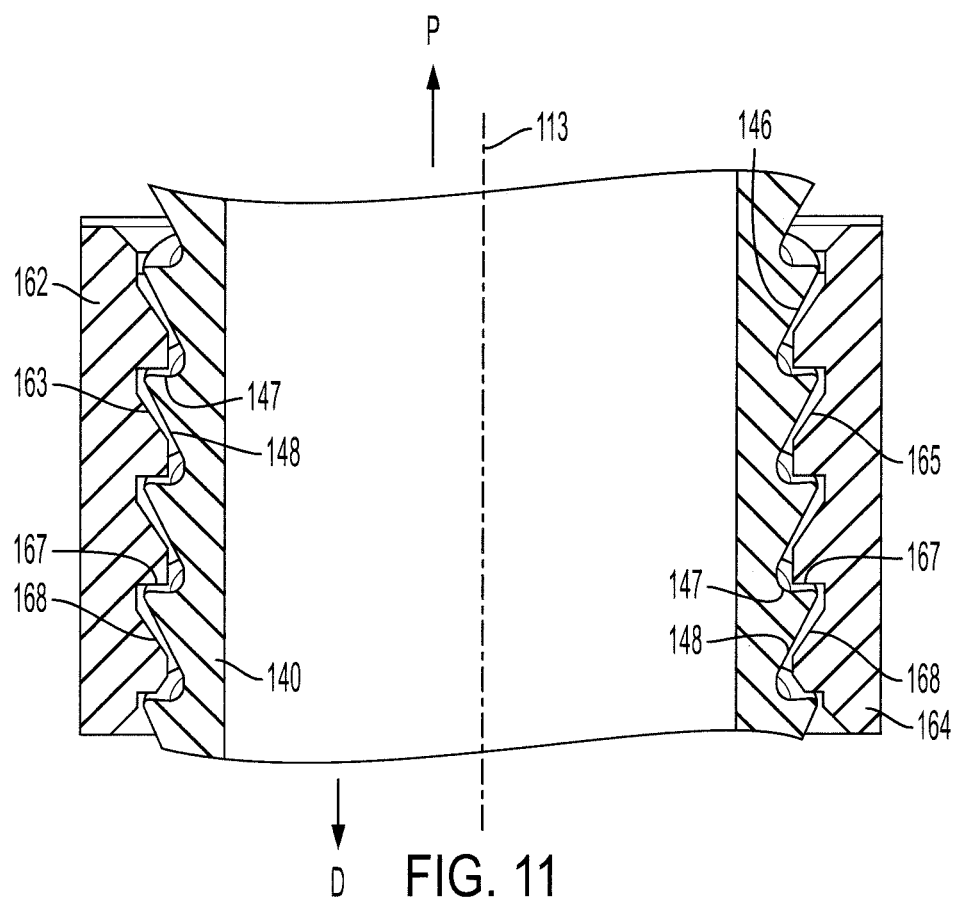
FIG. 11 is an enlarged truncated cross sectional view of elements of the ratchet assembly of FIG. 8.

Referring to FIG. 11, first ratchet surfaces 163, 165 define a plurality of undercuts 167 separated by ramps 168. Second ratchet surface 146 defines a plurality of ledges 147 separated by inclined faces 148. The term "inclined", as used in the context of the ratchet surfaces, refers to a surface that extends transversely to longitudinal axis 113 of housing 110. The shapes of ledges 147 and inclined faces 148 conform to the shapes of undercuts 167 and ramps 168. In this arrangement, first and second ratcheting blocks 162, 164 are radially displaceable relative to longitudinal axis 113 between a ratcheting position and a release position. In the ratcheting position, first ratchet surfaces 163, 165 mate with second ratchet surface 146. In the release position, first ratchet surfaces 163, 165 are radially separated and disengaged from second ratchet surface 146. FIG. 11 shows first ratchet surfaces 163, 165 mated with second ratchet surface 146 in the ratcheting position. In this mode, the ledges 147 abut the undercuts 167 in an axial direction to prevent shaft 140 from moving in the proximal direction, i.e. away from the detent tabs 126.

Ratchet assemblies according to the present disclosure can include one or more components for toggling ratcheting blocks 162, 164 between the ratcheting position and the release position. For example, ratchet assemblies according to the present disclosure can include one or more buttons, levers, slides or other structures that displace ratcheting blocks 162, 164 into and out of engagement with one another. Referring back to FIGS. 8-10, ratchet assembly 160 includes a first release button 172 and a second release button 174 diametrically opposed to the first release button relative to longitudinal axis 113. First release button 172 slidingly engages first ratcheting block 162 and second ratcheting block 164 to toggle the first ratcheting block and second ratcheting block between the ratcheting position and release position. Second release button 174 slidingly engages opposite sides of first ratcheting block 162 and second ratcheting block 164 to toggle the first ratcheting block and second ratcheting block between the ratcheting position and release position.

FIG. 9 shows first and second release buttons 172, 174 engaging first and second ratcheting blocks 162, 164 in the ratcheting position. In this position, first and second release buttons 172, 174 are positioned farther apart, allowing first and second ratcheting blocks 162, 164 to be closer together and mate with shaft 140. This corresponds to the first device configuration mentioned above. FIG. 10 shows first and second release buttons 172, 174 engaging first and second ratcheting blocks 162, 164 in the release position. In this position, first and second release buttons 172, 174 are pressed radially inwardly and closer together, displacing ratcheting blocks 162, 164 radially outwardly and out of engagement with shaft 140. This corresponds to the second device configuration mentioned above.

First release button 172 has a first portion 173 that projects outside of housing 110. First release button 172 also has a second portion 175 that extends into longitudinal passage 111 into engagement with first and second ratcheting blocks 162, 164. Similarly, second release button 174 has a first portion 177 that projects outside of housing 110. Second release button 174 also has a second portion 179 that extends into longitudinal passage 111 into engagement with first and second ratcheting blocks 162, 164.

Ratchet assembly 160 further includes a biasing mechanism 180 that biases first and second ratcheting blocks 162, 164 in the ratcheting position. Biasing mechanism 180 includes a first spring element 182 disposed between housing 110 and first ratcheting block 162 under stored energy. Biasing mechanism 180 also includes a second spring element 184 disposed between housing 110 and second ratcheting block 164 under stored energy. First and second spring elements 182, 184 exert biasing forces on first and second ratcheting blocks 162, 164 respectively to urge the ratcheting blocks toward the ratcheting position where they releasably engage shaft 140. In this arrangement, first and second spring elements 182, 184 provide an auto-locking ratchet assembly in which the rod persuader is automatically returned to a ratcheting mode after first and second release buttons 172, 174 are released.

First and second release buttons 172, 174 have respective edges that engage corresponding faces on first and second ratcheting blocks 162, 164. In particular, first release button 172 includes a first abutment edge 172A and a second abutment edge 172B. Second release button 174 includes a third abutment edge 174A and a fourth abutment edge 174B. First ratcheting block 162 has a first abutment face 162A that slidingly engages first abutment edge 172A, and a second abutment face 162B that slidingly engages third abutment edge 174A. Finally, second ratcheting block 164 has a third abutment face 164A that slidingly engages second abutment edge 172B, and a fourth abutment face 164B that slidingly engages fourth abutment edge 174B.

Abutment edges 172A, 172B, 174A, 174B and abutment faces 162A, 162B, 164A, 164B are arranged relative to one another such that pressing first and/or second release buttons 172, 174 radially inwardly causes first and second ratcheting blocks 162, 164 to spread apart into the release position. In particular, first release button 172 can be depressed radially inwardly toward longitudinal axis 113. As first release button 172 moves inwardly, it acts as a wedge between first and second ratcheting blocks 162, 164 and spreads them apart. Similarly, second release button 174 can be depressed radially inwardly toward longitudinal axis 113. As second release button 174 moves inwardly, it also acts as a wedge between first and second ratcheting blocks 162, 164 and spreads them apart. Therefore, pressing the first and/or second release buttons 172, 174 radially inwardly causes the first and second ratcheting blocks 162, 164 to move outwardly to the release position against the biasing forces of first and second spring elements 182, 184, respectively.

When first and second ratcheting blocks 162, 164 are in the ratcheting position, shown in FIG. 9, second ratchet surface 146 on shaft 140 mates with first ratchet surfaces 163, 165 of first and second ratcheting blocks 162, 164, respectively. First ratcheting surfaces 163, 165 are helical thread segments as noted above. Second ratcheting surface 164 is a helical thread adapted to mate with the helical thread segments on the first ratcheting surfaces 163, 165. This creates a threaded engagement between first and second ratcheting blocks 162, 164 and shaft 140, in which the shaft is axially displaceable toward the proximal housing end 112 and toward distal housing end 114 in response to rotation of the shaft relative to housing 110.

Shaft 140 is also axially displaceable toward the distal housing end 114 in response to axial force applied to shaft 110. However, shaft 140 is locked against axial displacement toward proximal housing end 112 in response to axial force. This one-way axial displacement can be appreciated from FIG. 11, which shows the orientations of inclined faces 148 and ramps 168. The arrow "P" points in the proximal direction toward proximal end 112 of housing 110, and the arrow "D" points in the distal direction toward distal end 114 of the housing. The orientations of inclined faces 148 and ramps 168 are such that movement of shaft 140 in the distal direction causes the inclined faces to bear outwardly against the ramps. This temporarily displaces ratcheting blocks 162, 164 radially outwardly against the biasing forces of first and second spring elements 182, 184. Once ledges 147 move past undercuts 167 in the distal direction, ratcheting blocks 162, 164 snap back into mated engagement with shaft 140. This locks shaft 140 against relative movement in the proximal direction when a proximal axial force is applied, due to the axial abutment between ledges 147 and undercuts 167 noted earlier.

Shaft 140 can be axially displaced in the distal direction by manually applying a distal axial force on the shaft. This can be done in the first device configuration or in the second device configuration. When first ratcheting surfaces 163, 165 and second ratcheting surface 164 are matingly engaged in the first device configuration, the inclined faces 148 push radially outwardly against the ramps 168 as shaft 140 moves in the distal direction relative to the ratcheting blocks 162, 164. This temporarily displaces ratcheting blocks 162, 164 radially outwardly against the biasing forces of first and second spring elements 182, 184. Once ledges 147 move past undercuts 167 in the distal direction, ratcheting blocks 162, 164 snap back into mated engagement with shaft 140. The biasing forces of first and second spring elements 182, 184 can be selected to provide a desired amount of resistance against outward displacement of ratcheting blocks 162, 164. The desired resistance can be selected so as to require a significant amount of axial force on shaft 140, thus preventing displacement of the shaft caused by inadvertent user contact with the shaft. This resistance to outward displacement of ratcheting blocks 162, 164 provides a mechanism for incremental advancement of anchor 150 in the distal direction which can be detected by an audible clicking sound each time the ratcheting blocks snap back into mating engagement with shaft 140.

Rod persuaders according to the present disclosure can feature different arm configurations that attach to polyaxial screw assemblies. For example, a rod persuader can have one arm mounted on a pivot hinge or other articulating joint that allows the arm to move relative to the housing. Referring back to FIGS. 3-6, first arm 122 is connected to housing 110 by a hinge 123. Hinge 123 permits first arm 122 to pivot radially outwardly to an open position and radially inwardly to a closed position. Hinge 123 has a pivot spring element 125. Pivot spring element 125, which can be a torsion spring or other type of biasing element, is connected between housing 110 and first arm 122 under stored energy. The stored energy exerts a biasing force on first arm 122 that biases the first arm toward the closed position.

First arm 122 is pivotable radially outwardly against the biasing force of pivot spring element 125 to an open position shown in FIG. 5. In this open position, first and second arms 122, 124 can be placed around a fixation rod and a rod receiver of a polyaxial screw assembly. Once the arms are placed around the fixation rod and rod receiver, first arm 122 can pivoted radially inwardly toward the longitudinal axis to a closed position shown in FIG. 6. Once first arm 122 is in the closed position, the arms can be pressed into cutouts in the polyaxial screw assembly to lock rod persuader 100 to the polyaxial screw assembly.

Rod persuaders according to the present disclosure can have one or more guiding structures that aid in aligning a fixation rod with the rod receiving channel of a polyaxial screw assembly. Often times, the rod persuader arms will be closed around a fixation rod, but the fixation rod will not be centered between the arms or aligned above the rod receiving channel of the polyaxial screw assembly.

In the present example, first and second arms 122, 124 include rod guiding surfaces. In particular, first arm 122 includes a first rod guiding surface 127 and second arm 124 includes a second rod guiding surface 129, as shown in FIG. 6. First and second rod guiding surfaces 127, 129 include rounded sections that converge inwardly toward the longitudinal axis, forming a funnel or rod-centering structure. In the event that a fixation rod is positioned off center with respect to first and second arms 122, 124 and contacts one of the rod guiding surfaces 127, 129, the fixation rod will be moved toward the center of gap 128 by the funnel structure as the fixation rod is advanced by anchor 150 into the rod receiving component. Concave distal edges 156, 157 of anchor 150 also provide a centering influence that guides the fixation rod to a centered position on longitudinal axis 113 so that the rod is received into the rod receiving component.

Rod persuaders according to the present disclosure can also have mechanisms that reinforce the clamped connection between the first and second arms and the polyaxial screw assembly during rod persuasion. In the present example, anchor 150 is axially displaceable along first and second arms 122, 124 between a proximal or raised position and a distal or lowered position. In the raised position, frame portion 152 is positioned adjacent to distal housing end 114. In the lowered position, frame portion 152 is positioned closer to detent tabs 126. The rectangular brace or sleeve 154 formed by frame portion 152 applies radially inward force on first and second arms 122, 124 and detent tabs 126 as anchor 150 is advanced toward the lowered position. This provides additional clamping force to reinforce the connection between rod persuader 100 and the polyaxial screw assembly.

Additional examples of rod persuaders according to the present disclosure will be described in the following paragraphs. Many structural and functional features of rod persuaders in the examples that follow are similar or identical to those of rod persuader 100 and/or rod persuader 1000. Some of these common features will not be repeated for brevity, with the understanding that features shown in the Figures that correspond to features described in rod persuader 100 and/or rod persuader 1000 have the same description.

Rod persuaders according to the present disclosure include features that allow the instrument to perform rod persuasion in conjunction with one or more other procedures, either at the same time that the rod persuasion is performed, or shortly before or after rod persuasion. This multi-functionality allows multiple procedures to be performed by one stand-alone instrument attached to the polyaxial screw assembly. This is advantageous because it avoids having to sterilize multiple instruments and keep them on hand at the operating table. It also avoids having to attach and detach multiple instruments to and from the polyaxial screw assembly during surgery.

Figure 12:
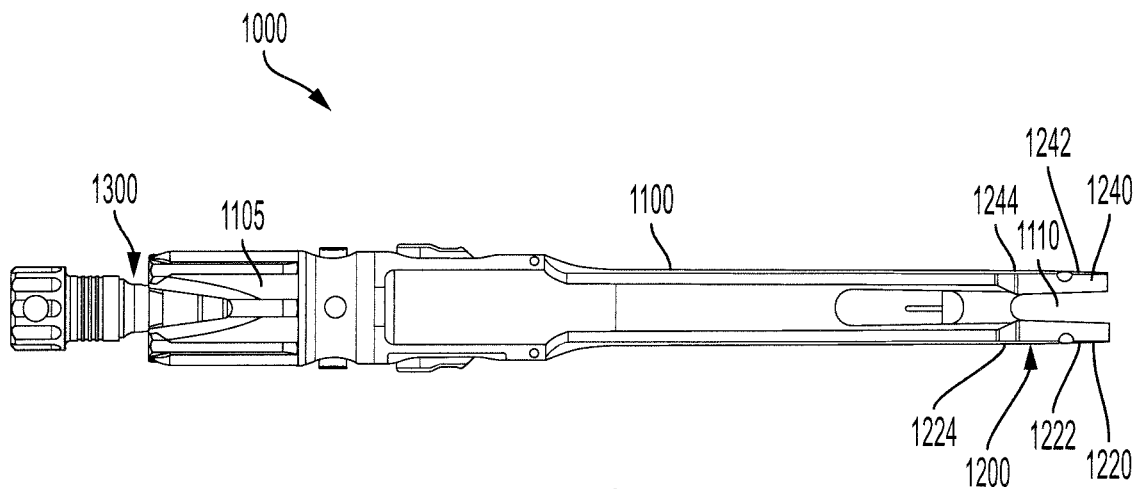
FIG. 12 is a side view of a sequential rod persuader instrument according to another example.

One example of a multi-functional rod persuader according to the present disclosure is rod persuader 1000 shown in FIG. 12. Rod persuader 1000 is configured to reposition or reorient a vertebral body so that the vertebral body is aligned with a fixation rod, similar to rod persuader 100. However, rod persuader 1000 also has features that facilitate "polylocking" and spinal "derotation".

Polylocking, as used herein, refers to a procedure that provisionally locks the position of a rod receiver relative to the position of a bone screw on a polyaxial screw assembly, without inserting a rod and locking screw (e.g. set screw) into the polyaxial screw assembly. This is performed as a temporary locking procedure that disables polyaxial rotation of the rod receiver about the head of the bone screw. Once polylocking is performed, the bone screw and rod receiver form a singular fixed construct, allowing adjustment force to be applied to both the rod receiver and bone screw in unison.

Derotation, as used herein, refers to a procedure for correcting abnormal spinal curvatures. In a derotation procedure, one or more instruments are used to apply bending moments to one or more polyaxial screw assemblies implanted in vertebral bodies. A bending moment induces rotational and translational movement of a vertebral body relative to adjacent bodies. Rotational and translational movement of vertebral bodies can be done in a coordinated manner to adjust the spinal curvature.

Rod persuader 1000 includes an elongated housing 1100 that defines a longitudinal passage 1110. An exterior portion of housing 1100 includes a grooved section 1105 configured to mate with couplers and counter-torque instruments. Housing 1100 also has a clamping assembly 1200 for attaching the housing to a polyaxial screw assembly. Clamping assembly 1200 includes a first arm 1220 and a second arm 1240 individually operable to clamp onto a polyaxial screw assembly and detach from a polyaxial screw assembly. First and second arms 1220, 1240 each define elongated apertures and include pivot arms that are pivotably mounted in the apertures. Clamping assemblies with pivot arms that can be used according to the present disclosure include, but are not limited to, the assemblies described in U.S. application Ser. No. 16/371,836, the content of which is incorporated by reference herein in its entirety.

In the present example, first arm 1220 includes a first pivot arm 1222 pivotably mounted in a first aperture 1224. Second arm 1240 includes a second pivot arm 1242 pivotably mounted in a second aperture 1244. First and second pivot arms 1222, 1242 are each pivotable between an attachment position and a release position. In the attachment position, first and second pivot arms 1222, 1242 are pivoted radially inwardly toward one another and into a position to attach rod persuader 1000 to an engagement structure, such as a bore, slot, cut-out or other type of void, on a polyaxial screw assembly. In the release position, first and second pivot arms 1222, 1242 are pivoted radially outwardly and away from one another to disengage the engagement structure on the polyaxial screw assembly. First and second pivot arms 1222, 1242 are each biased toward their respective attachment position by biasing elements that engage proximal ends of each pivot arm. Biasing elements may be in the form of leaf springs, wave springs, torsion springs, coil springs, spring washers and other biasing elements that store and release energy upon application and removal of force.

Figure 13:
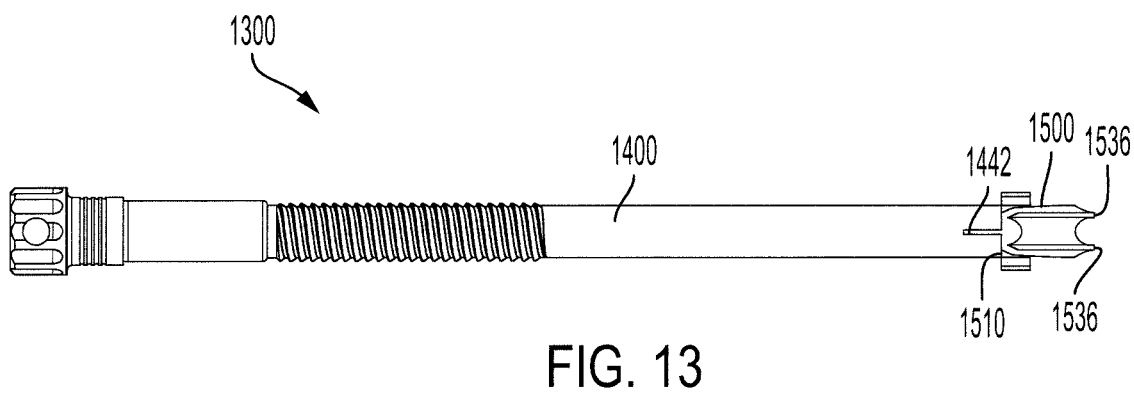
FIG. 13 is a side view of components of the rod persuader instrument according to FIG. 12.
Figure 14:
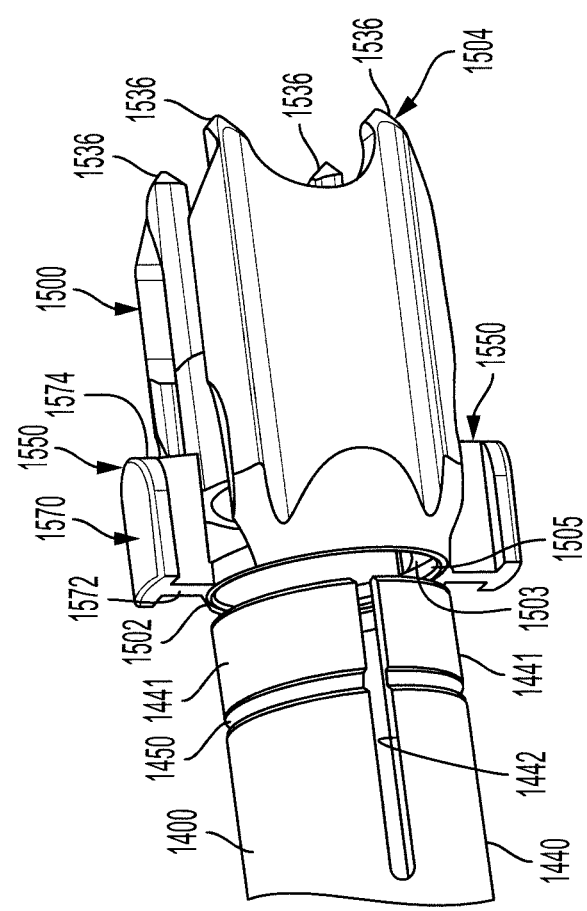
FIG. 14 is an enlarged and exploded perspective view of components of the rod persuader instrument according to FIG. 12.

Referring now to FIGS. 13 and 14, rod persuader 1000 further includes a rod persuading assembly 1300. Rod persuading assembly 1300 includes a shaft 1400 coupled to an anchor 1500. Shaft 1400 has a distal end 1440 that defines diametrically opposed slots 1442 extending in an axial direction. Slots 1442 thus divide distal end 1440 into distal end segments 1441. A circumferential groove 1450 extends around the exterior of distal end segments 1441.

Anchor 1500 has a proximal end 1502 defining a socket 1503 adapted to receive distal end segments 1441 of shaft 1400. Socket 1503 forms an annular rim 1505 that extends radially inwardly toward the center of the socket, forming a reduced diameter section at the opening into the socket. The inner diameter of socket 1503 inside rim 1505 is smaller than the outer diameter of distal end segments 1441 of shaft 1400 when the distal end segments are relaxed. The inner diameter of socket 1503 inside rim 1505 is substantially equal to or slightly larger than the outer diameter of distal end segments 1441 inside circumferential groove 1450, however.

Distal end segments 1441 are configured to act as leaf springs that bend or converge toward one another in response to radial compression when the distal end segments are inserted through rim 1505 into socket 1503. As distal end segments 1441 advance past rim 1505, the distal end segments are compressed inwardly toward one another into slots 1442 and remain compressed under stored energy. When circumferential groove 1450 aligns with rim 1505, the distal end segments 1441 release the stored energy and snap radially outwardly so that the rim becomes captured inside the circumferential groove. Walls inside circumferential groove 1450 prevent further axial movement of shaft 1400 relative to socket 1503 in either a proximal or distal direction. Therefore, circumferential groove 1450 lockingly engages rim 1505 to couple shaft 1400 to anchor 1500.

Rim 1505 and circumferential groove 1450 form an axially fixed, rotatable coupling 1510. When rod persuader 1000 is fully assembled, the orientation of anchor 1500 is fixed relative to the orientation of housing 1100 due to alignment features and anti-splaying elements which will be described. The orientation of shaft 1400 is not fixed relative to housing 1100, however. As such, shaft 1400 is permitted to rotate relative to housing 1100 and anchor 1500 to axially displace the anchor in longitudinal passage 1110, while the orientation of the anchor remains unchanged.

Anchors according to the present disclosure can include one or more polylocking features configured to provisionally lock a rod receiver relative to the head of a polyaxial screw assembly. U.S. application Ser. No. 16/371,836, incorporated by reference above, describes polyaxial screw assemblies and polylocking features that can be used with rod persuaders of the present disclosure.

Figure 15:
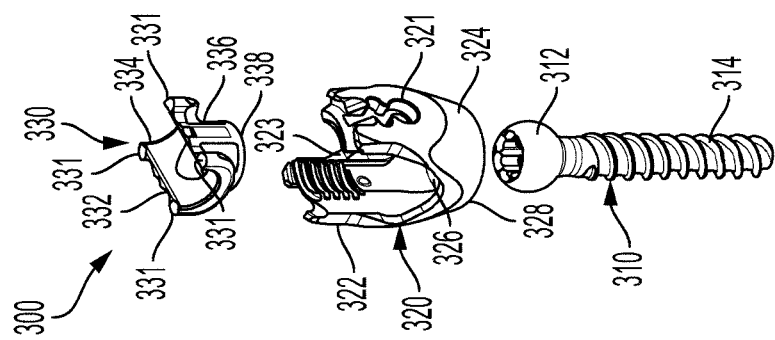
FIG. 15 is an exploded perspective view of a polyaxial screw assembly that can be used with rod persuader instruments according to the present disclosure.
Figure 16:
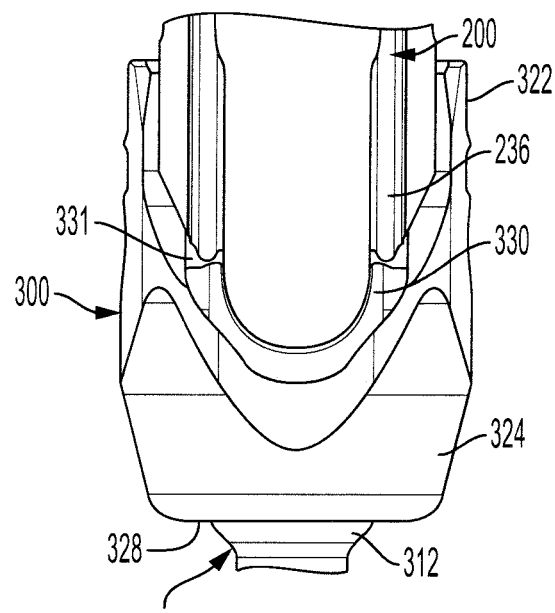
FIG. 16 is an enlarged cross section view of the rod persuader instrument according to FIG. 12 engaged with the polyaxial screw assembly of FIG. 15 in a polylocking procedure.

Referring now to FIGS. 14-16, polylocking features will be described in conjunction with a polyaxial screw assembly 300. Anchor 1500 includes a distal end 1504 with polylocking features that are configured to provisionally lock polyaxial screw assembly 300.

Polyaxial screw assembly 300 includes a polyaxial bone screw 310 with a spherical shaped screw head 312 and threaded shank 314, as shown in FIG. 15. Bone screw 310 is configured to be received in rod receiver 320. Rod receiver 320 has an upper portion 322 that defines a U-shaped channel 323 to receive an elongated fixation element, such as a spinal rod. Rod receiver 320 also has a lower portion 324 that defines a seat 326 in its interior and a through-hole 328. Seat configurations can have various geometries, such as a spherical or conical shape. In the present example, seat 326 is conical. Through-hole 328 has a diameter that is smaller than the diameter of screw head 312. Rod receiver 320 is therefore configured to receive bone screw 320 in a seated arrangement, with screw head 312 seated in conical seat 326, and with threaded shank 314 projecting out of through-hole 328.

Rod receiver 320 has a pair of diametrically opposed cut-outs 321 that are open on the exterior of the rod receiver, and that extend into the wall of the rod receiver. Cut-outs 321 have irregular shapes that conform to the irregular shapes of locking tabs provided on first and second pivot arms 1222, 1242 of rod persuader 1000.

Polyaxial screw assembly 300 also includes an insert 330. Insert 330 has an upper portion 332 that defines a U-shaped recess 334 to receive an elongated fixation element, such as a spinal rod. Insert 330 also has a lower portion 336 with a spherical shaped concavity 338. When polyaxial screw assembly 300 is assembled, insert 330 is positioned in rod receiver 320 in a position proximal to screw head 312. In this position, recess 334 is positioned to receive an elongated fixation element, such as a spinal rod, and concavity 338 is positioned to bear against and frictionally engage screw head 312.

Distal end 1504 of anchor 1500 includes four pusher posts 1536, as seen in FIG. 14. Pusher posts 1536 are configured to apply axial force to insert 330 when anchor 1500 is advanced into rod receiver 320 and provisionally lock the position of the rod receiver relative to the screw head 312. Each pusher post 1536 is positioned to engage a landing 331 on the top of insert 320, as shown in FIG. 16. Axial force on landings 331 compresses insert 330 into frictional engagement with screw head 312 of bone screw 310. The frictional engagement is sufficient to stabilize the rod receiver 320 on screw head 310 so that the rod receiver does not pivot or "flop" on the bone screw.

Anchors according to the present disclosure can also include one or more features that prevent splaying from occurring, i.e. anti-splaying features. The term "splaying", as used herein, refers to an outward deflection of clamping arms or pivot arms of a housing when another instrument is advanced through the housing. Splaying is undesirable because it can cause the clamping arms or pivot arms to disconnect from the polyaxial screw assembly, interrupting a surgical procedure. Thus, an "anti-splaying" feature, as used herein, refers to any feature that holds clamping arms or pivot arms in their locked positions on a rod receiver and prevents the arms from splaying.

In the present example, proximal end 1502 of anchor 1500 has a first pair of anti-splaying features in the form of locking rails 1550. Each locking rail 1550 has a T-shaped body 1570 comprising a stem portion 1572 that extends outwardly from anchor 1500 and a flange portion 1574 that extends generally perpendicular to stem portion 1572.

Figure 17A:
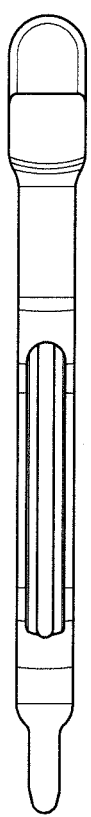
FIG. 17A is a front view of a clamping arm of the rod persuader instrument according to FIG. 12.
Figure 17B:
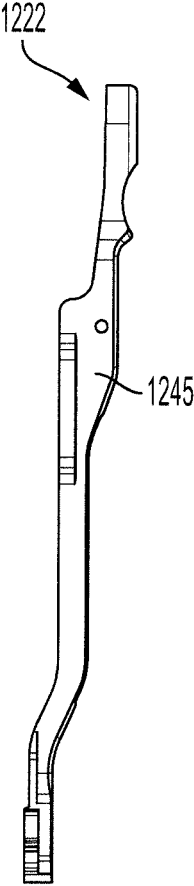
FIG. 17B is a side view of the clamping arm of the rod persuader instrument according to FIG. 12.
Figure 17C:
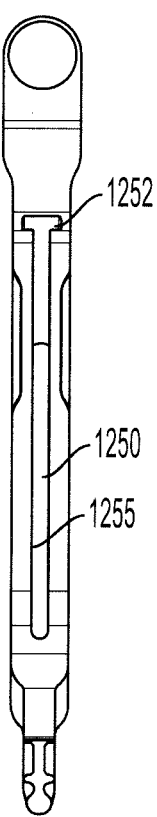
FIG. 17C is a rear view of the clamping arm of the rod persuader instrument according to FIG. 12.

The details of first pivot arm 1222 and second pivot arm 1242 will now be described in more detail with reference to FIGS. 17A-17C. First and second pivot arms 1222, 1224 are identically configured. Therefore, the features of first pivot arm 1222 will be described with the understanding that identical features are present on second pivot arm 1224.

First pivot arm 1222 defines a dog leg section 1245 and an anti-splaying slot 1250. Each anti-splaying slot 1250 forms an aperture 1252 in its respective dog leg section 1245. Each aperture 1252 is adapted to axially receive one of the locking rails 1550 (shown in FIG. 14) and allow the locking rail to slide axially to the distal end of the pivot arm. Anti-splaying slots 1250 also define openings 1255 that are open to longitudinal passage 1110. Openings 1255 receive stem portions 1572 of locking rails 1550 when the locking rails are inserted into the first and second pivot arms 1222, 1242. Locking rails 1550 are axially positioned on anchor 1500 so that when the anchor is advanced as far as possible into a polyaxial screw assembly to engage an insert, the locking rails maintain pivot arms 1222, 1242 in a straight configuration with their locking tabs firmly fixed in cut-outs or other engagement features on the rod receiver. This prevents the distal ends of pivot arms 1222, 1242 from splaying or bending outwardly and disengaging from the polyaxial screw assembly.

Figure 18:
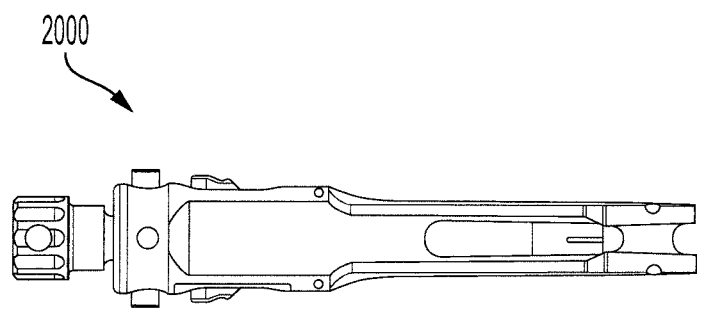
FIG. 18 is a side view of a sequential rod persuader instrument according to another example.

FIG. 18 shows a rod persuader 2000 according to another embodiment of the disclosure. Rod persuader 2000 is substantially identical to rod persuader 1000 but has a shorter axial length than rod persuader 1000. In addition, rod persuader 2000 does not have the grooved section 1105 configured to mate with couplers and counter-torque instruments. The shorter axial length of rod persuader 2000 is beneficial when many rod persuaders are attached to the spine at the same time. The shorter lengths reduce the stress on the spine caused by the combined weight of multiple instruments. In addition, the shorter lengths result in fewer visual obstructions above the spine.

Figure 19:
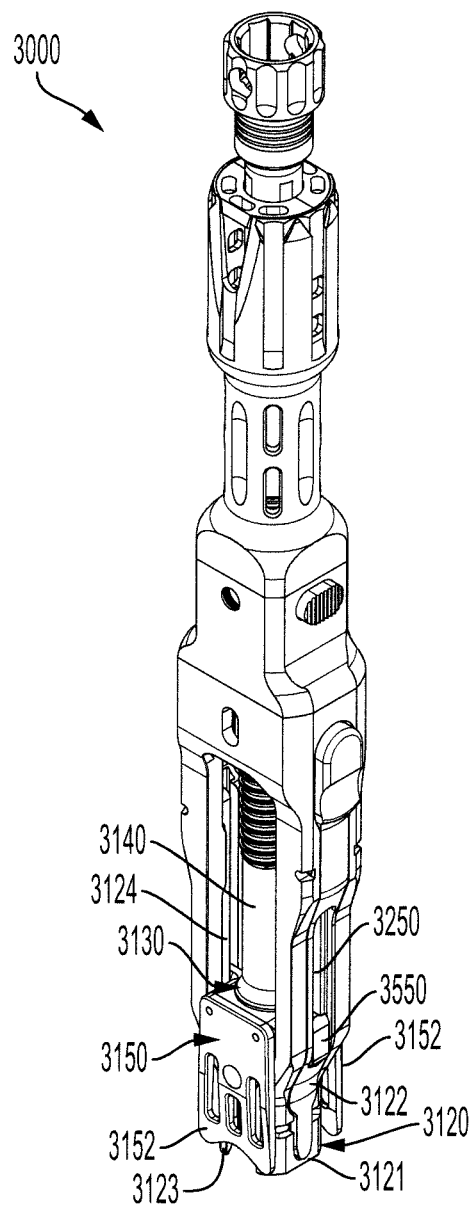
FIG. 19 is a perspective view of a sequential rod persuader instrument according to another example.

FIG. 19 shows a rod persuader 3000 according to another embodiment of the disclosure. Rod persuader 3000 is similar to rod persuader 1000, but has a different vertebral anchor clamping assembly 3120. Clamping assembly 3120 includes first and second sleeve portions 3121, 3123. This arrangement provides a wider opening and connection mechanism that can be lowered more easily onto a polyaxial screw assembly.

A first clamping arm 3122 is pivotably mounted in first sleeve portion 3121, and a second clamping arm 3124 is pivotably mounted in second sleeve portion 3123. Rod persuader 3000 also has a rod persuader assembly 3130 featuring an anchor 3150 with two anchor plates 3152. Anchor plates 3152 are axially displaceable on either side of first and second sleeve portions 3121, 3123. Rod persuader assembly 3130 also includes a shaft 3140 with anti-splaying features in the form of locking rails 3550, one of which is visible extending in an anti-splaying slot 3250 in first clamping arm 3122.

Figures 20, 21:
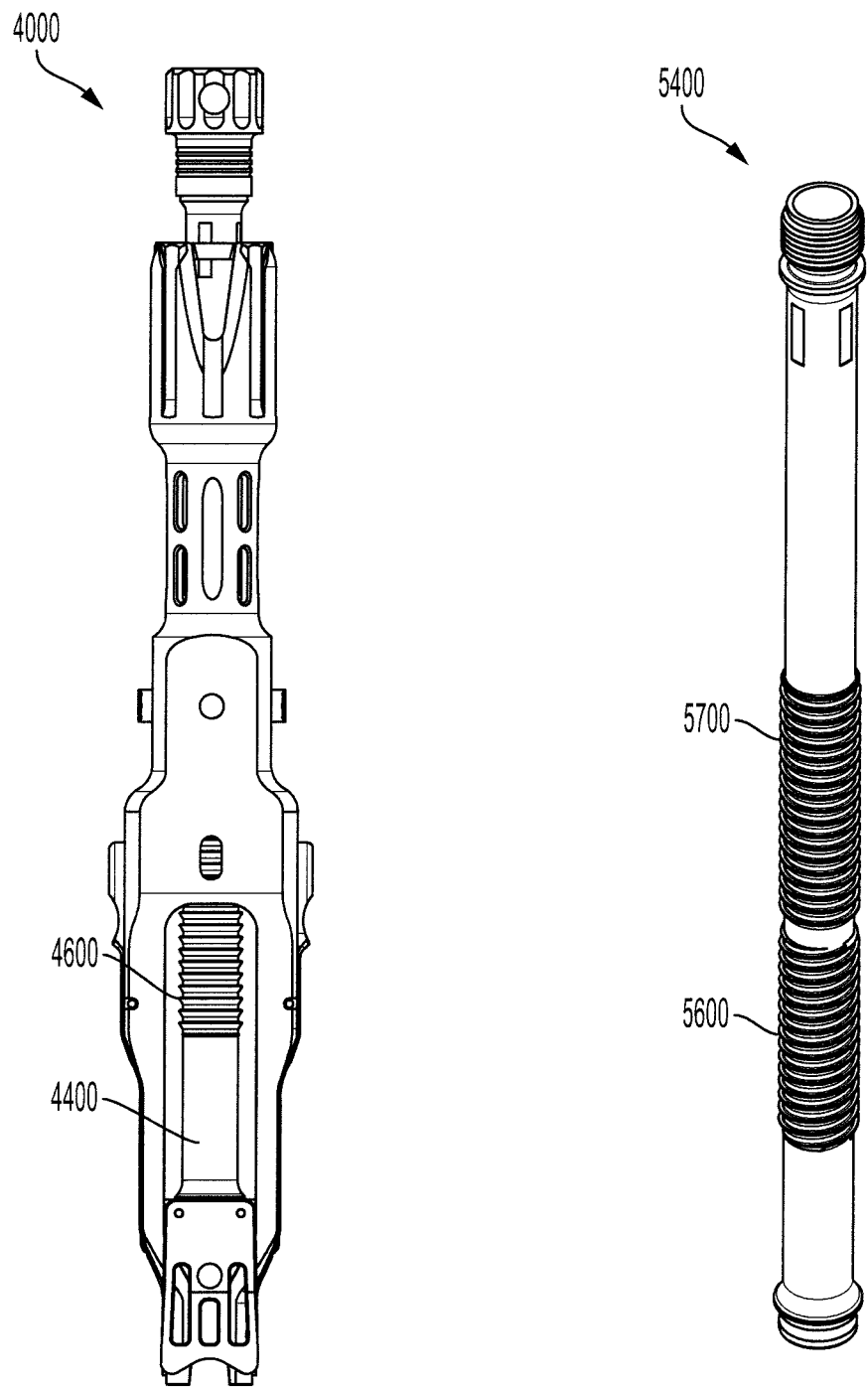
FIG. 20 is a side view of a sequential rod persuader instrument according to another example.
FIG. 21 is a perspective view of a shaft of a rod persuader instrument according to another example.

Referring now to FIG. 20, a rod persuader 4000 is shown according to another example. Rod persuader 4000 has an elongated shaft 4400 that is similar to the shafts of the previous examples, but the shaft features a linear arrangement of ratchet teeth 4600 that follow a saw tooth configuration (i.e. a series of separate circumferential teeth) rather than a helical thread arrangement (i.e. one continuous helical thread). This saw tooth configuration can provide controlled shaft displacement and free shaft displacement like a helical thread, and may be desirable where mechanical advantage is not a requirement.

Referring now to FIG. 21, an elongated shaft 5400 is shown according to another example. Shaft 5400 is similar to the shafts of the previous examples, but combines a first set of ratchet teeth 5600 having a helical thread arrangement with a second set of ratchet teeth 5700 having a saw tooth configuration. This configuration provides a controlled, one-way shaft displacement with mechanical advantage up to a certain point. As shaft 5400 is initially advanced through ratchet blocks, first set of ratchet teeth 5600 can engage the ratchet blocks to allow the shaft to be driven via the threaded engagement under mechanical advantage. After the first set of ratchet teeth 5600 pass the ratchet blocks, the ratchet blocks can engage the second set of ratchet teeth 5700 to continue advancement. It will be appreciated that the first and second sets of ratchet teeth 5600, 5700 can be reversed, such that the ratchet blocks initially engage the ratchet teeth with a saw tooth configuration before engaging ratchet teeth with a thread arrangement. The two ratchet teeth configurations can be used in any combination, with the sections having the same axial length or different axial lengths so as to apply appropriate forces for a given application.

Although this description makes reference to specific embodiments and illustrations, the invention is not intended to be limited to the details shown. For example, embodiments that feature a ratchet assembly need not have a pair of ratcheting blocks that control movement of the shaft and anchor, but could feature a ratchet assembly with a single ratcheting block that engages the shaft on one side of the longitudinal axis. Alternatively, the ratchet assembly could have three or more ratcheting blocks that are arranged around the shaft. Moreover, the ratchet assembly need not have a pair of diametrically opposed buttons that toggle the ratchet assembly between the release position and ratcheting position, but could feature a single button acting as a wedge between two ratcheting blocks. Therefore, rod persuaders according to the present disclosure can feature any number of ratcheting blocks and release structures, and are not limited to the examples shown.

Accordingly, the present disclosure encompasses various modifications and combinations of features present in the specific embodiments and illustrations described herein, including variations and combinations that may be made within the scope and range of equivalents of the originally filed claims.

What is claimed:

1. A persuader instrument for advancing a fixation rod into a rod receiving channel of a vertebral implant, the persuader instrument comprising:
   a housing comprising a proximal housing end and a distal housing end, the housing defining a longitudinal passage extending between the proximal housing end and distal housing end, the housing further defining a longitudinal axis extending through the longitudinal passage;
   a first arm and a second arm, the first and second arms comprising detents configured for detachable connection to the vertebral implant;
   an anchor comprising a fixation rod engagement surface;
   a shaft comprising a proximal shaft end and a distal shaft end, the distal shaft end coupled to the anchor in an axially fixed but rotatable connection, with the shaft being axially displaceable through the longitudinal passage of the housing to axially displace the anchor; and
   an auto-locking ratchet assembly in releasable engagement with the shaft, the auto-locking ratchet assembly operable to control axial displacement of the shaft through the longitudinal passage of the housing,
   wherein the auto-locking ratchet assembly comprises at least one ratcheting block that releasably engages the shaft, and
   wherein the auto-locking ratchet assembly comprises at least one release button, the at least one release button being movable relative to the at least one ratcheting block.

2. The persuader instrument of claim 1, wherein the at least one ratcheting block comprises a first ratchet surface and the shaft comprises a second ratchet surface in releasable engagement with the first ratchet surface.

3. The persuader instrument of claim 2, wherein one of the first ratchet surface and the second ratchet surface comprises a plurality of ledges separated by inclined faces, and the other of the first ratchet surface and the second ratchet surface comprises a plurality of undercuts separated by ramps.

4. The persuader instrument of claim 3, wherein the at least one ratcheting block is radially displaceable relative to the longitudinal axis between a ratcheting position in which the first ratchet surface matingly engages with the second ratchet surface, and a release position, in which the first ratchet surface is radially separated and disengaged from the second ratchet surface.

5. The persuader instrument of claim 4, wherein the plurality of ledges axially abut the plurality of undercuts when the at least one ratcheting block is in the ratcheting position to prevent the shaft from moving toward the proximal housing end.

6. The persuader instrument of claim 4, wherein the at least one release button toggles the at least one ratcheting block between the ratcheting position and the release position.

7. The persuader instrument of claim 6, further comprising at least one spring element in engagement with the at least one ratcheting block, the at least one spring element disposed between the housing and the at least one ratcheting block under stored energy that exerts a biasing force on the at least one ratcheting block to urge the at least one ratcheting block toward the ratcheting position.

8. The persuader instrument of claim 7, wherein the at least one release button is movable to a depressed position to move the at least one ratcheting block to the release position against the biasing force of the spring element.

9. The persuader instrument of claim 4, wherein when the at least one ratcheting block is in the ratcheting position, the shaft is axially displaceable toward the proximal end of the housing and toward the distal end of the housing in response to rotation of the shaft relative to the housing.

10. The persuader instrument of claim 4, wherein when the at least one ratcheting block is in the ratcheting position, the shaft is axially displaceable toward the distal housing end in response to axial force applied to the shaft, but is locked against axial displacement toward the proximal housing end in response to axial force.

11. The persuader instrument of claim 2, wherein the first and second ratchet surfaces comprise threads.

12. The persuader instrument of claim 2, wherein the first and second ratchet surfaces comprise ratchet teeth that follow a saw tooth configuration.

13. The persuader instrument of claim 2, wherein the first and second ratchet surfaces each comprise a first section having threads and a second section having ratchet teeth that follow a saw tooth configuration.

14. The persuader instrument of claim 1, wherein the at least one release button comprises a first abutment surface and the at least one ratcheting block comprises a second abutment surface that slidingly engages the first abutment surface.

15. The persuader instrument of claim 1, wherein the at least one release button has a first portion that projects outside of the housing and a second portion that extends into the longitudinal passage into engagement with the at least one ratcheting block.

16. The persuader instrument of claim 1, wherein at least one of the first and second arms is pivotable radially outwardly from the longitudinal axis to an open position, and pivotable radially inwardly toward the longitudinal axis to a closed position.

17. The persuader instrument of claim 16, wherein said at least one of the first and second arms is connected to the housing by a hinge comprising a pivot spring element, the pivot spring element connected between the housing and said at least one of the first and second arms under stored energy that biases said at least one of the first and second arms toward the closed position.

18. The persuader instrument of claim 1, wherein the first arm comprises a first rod guiding surface and the second arm comprises a second rod guiding surface, the first and second rod guiding surfaces converging inwardly toward the longitudinal axis.

19. The persuader instrument of claim 18, wherein the first and second rod guiding surfaces comprise rounded sections.

20. The persuader instrument of claim 1, wherein the anchor comprises a frame portion arranged around the first and second arms.

21. The persuader instrument of claim 20, wherein the anchor is axially displaceable between a raised position and a lowered position, the frame portion being positioned closer to the detents in the lowered position to apply a radially inward clamping force to distal ends of the first and second arms.

22. The persuader instrument of claim 20, wherein the first and second arms comprise rail portions on which the frame portion of the anchor is slidably arranged, and detent portions that comprise the detents, the detent portions arranged radially inwardly relative to the rail portions.

23. The persuader instrument of claim 1, wherein the anchor comprises one or more polylocking features.

24. The persuader instrument of claim 1, wherein the anchor comprises one or more anti-splaying elements.

25. The persuader instrument of claim 24, wherein the first arm and the second arm comprise one or more anti-splaying features that cooperate with the one or more anti-splaying elements of the anchor.

26. A persuader instrument for advancing a fixation rod into a rod receiving channel of a vertebral implant, the persuader instrument comprising:
 a housing comprising a proximal housing end and a distal housing end, the housing defining a longitudinal passage extending between the proximal housing end and distal housing end, the housing further defining a longitudinal axis extending through the longitudinal passage;
 a first arm and a second arm, the first and second arms comprising detents configured for detachable connection to the vertebral implant;
 an anchor comprising a fixation rod engagement surface;
 a shaft comprising a proximal shaft end and a distal shaft end, the shaft being hollow and forming a hollow bore that extends from the proximal shaft end to the distal shaft end, the distal shaft end rotatably coupled to the anchor, with the shaft being axially displaceable through the longitudinal passage of the housing to axially displace the anchor; and
 an auto-locking ratchet assembly in releasable engagement with the shaft, the auto-locking ratchet assembly operable to control axial displacement of the shaft through the longitudinal passage of the housing,
 wherein the auto-locking ratchet assembly comprises at least one ratcheting block that releasably engages the shaft, and
 wherein the auto-locking ratchet assembly comprises at least one release button, the at least one release button in slidable engagement with the at least one ratcheting block.

27. The persuader instrument of claim 26, wherein the at least one release button toggles the at least one ratcheting block between a ratcheting position and a release position.

* * * * *